United States Patent [19]

McMichael

[11] Patent Number: 5,726,160
[45] Date of Patent: Mar. 10, 1998

[54] METHODS FOR TREATING RESPIRATORY DISEASE

[75] Inventor: John McMichael, Delanson, N.Y.

[73] Assignee: Milkhaus Laboratories, Inc., Delanson, N.Y.

[21] Appl. No.: 755,092

[22] Filed: Nov. 22, 1996

Related U.S. Application Data

[63] Continuation of Ser. No. 421,232, Apr. 13, 1995, abandoned.

[51] Int. Cl.$^6$ ............................ A01N 43/04; A61K 31/70
[52] U.S. Cl. ...................... 514/44; 514/2; 514/47; 514/50; 536/22.1; 424/9.2
[58] Field of Search ....................... 514/44, 47, 2, 514/50; 536/22.1; 424/9.2

[56] References Cited

U.S. PATENT DOCUMENTS

| | | | |
|---|---|---|---|
| 5,240,846 | 8/1993 | Collins et al. | 435/240.1 |
| 5,292,498 | 3/1994 | Boucher, Jr. | 424/45 |
| 5,420,116 | 5/1995 | Puchelle et al. | 514/47 |
| 5,470,838 | 11/1995 | von Borstel et al. | 514/50 |

FOREIGN PATENT DOCUMENTS

| | | |
|---|---|---|
| WO 92/11016 | 7/1992 | WIPO . |
| WO 96/40059 | 12/1996 | WIPO . |
| WO 97/05195 | 2/1997 | WIPO . |

OTHER PUBLICATIONS

Miller, Science, 269, 1995, 1050–1055.
Ledley, Human Gene Therapy, 6, 1995, 1129–1144.
Rosenfeld et al., Science, 252, 1991, 431–434.
Ledley, Curr. Opin. Biotechnology, 5, 1994, 626–636.
Canonico et al., Clin. Res., 39 (2), 1991, 219 A.

*Primary Examiner*—Jasemine C. Chambers
*Assistant Examiner*—Jill D. Schmuck
*Attorney, Agent, or Firm*—Marshall, O'Toole, Gerstein, Murray & Borun

[57] ABSTRACT

Methods for treating respiratory disease, including cystic fibrosis, emphysema, bronchitis, and sinusitis are presented. Methods comprise administering to a patient an effective amount of DNA in a manner so as not to effect gene transfer and expression.

7 Claims, No Drawings

METHODS FOR TREATING RESPIRATORY DISEASE

This is a continuation of U.S. application Ser. No. 08/421,232, filed Apr. 13, 1995, now abandoned.

FIELD OF THE INVENTION

The present invention relates to methods for treatment of pulmonary disorders.

BACKGROUND OF THE INVENTION

The present invention provides methods for treatment of pulmonary diseases. Such diseases, including cystic fibrosis, emphysema, chronic bronchitis, sinusitis, and the common cold, have in common bronchial or sinus congestion, production of large amounts of sputum, and the possibility of secondary bacterial infection requiring antibiotic therapy. The most serious of those diseases is cystic fibrosis, a genetic disorder of exocrine function characterized by abnormally viscous mucus secretions leading to chronic pulmonary obstruction, pancreatic insufficiency and elevated sweat sodium and chloride levels. Cystic fibrosis is often fatal. The viscosity of sputum produced by cystic fibrosis patients is thought to be due to its high content of DNA. Diseases such as bronchitis, emphysema, sinusitis, and the common cold are generally less severe than cystic fibrosis, but those diseases also may result in production of large amounts of sputum. As with cystic fibrosis, other pulmonary diseases frequently lead to secondary bacterial infections.

Treatment of pulmonary diseases generally requires antibiotic therapy which is frequently ineffective. Recently, however, cystic fibrosis has been treated using DNase. The rationale for such therapy is that degrading DNA in sputum reduces the viscosity of the sputum and results in an increased ability of the patient to evacuate sputum from the lungs and nasal passages. However, no known report advocates using DNA itself as a treatment for any pulmonary infection.

SUMMARY OF THE INVENTION

The present invention provides methods for treating respiratory illness. In a preferred embodiment, the invention provides methods for reducing congestion in a patient having a respiratory illness. Methods of the invention result in reduced viscosity of mucus, increased productivity of respiratory congestion and reduced accumulation of mucus in the respiratory and nasal passages.

Methods of the invention comprise administration to a patient suffering from respiratory congestion an effective amount of DNA. The DNA is preferably provided in an amount ranging from about 0.00012 mg to about 0.003 mg and is preferably formulated in a liquid vehicle and provided at a concentration of approximately 0.0006 mg as single drops. A preferred route of administration is sublingual, but other routes, such as intravenous, intramuscular, and intrathecal are expected to work. DNA for use in the present invention may be prokaryotic DNA or eukaryotic DNA and may be formulated in a number of pharmaceutically-acceptable vehicles, including water, saline, albumin, and dextrose.

Additional aspects and advantages of the invention will become apparent upon consideration of the following detailed description thereof.

DETAILED DESCRIPTION OF THE INVENTION

The present invention provides methods for treating patients with pulmonary disease by administering to such patients a small amount of DNA.

Presently claimed methods are useful for treating pulmonary congestion in patients having any disease in which mucus production is a symptom. Methods of the invention are especially effective in treating diseases wherein viscous mucus or sputum is produced and becomes lodged in a patient's respiratory tract. In those cases, methods of the invention reduce production of DNA in a patient's mucus secretions and thereby render mucus less viscous, allowing for increased production away from the respiratory tract.

Methods according to the invention have been tested in clinical trials with human patients having various respiratory disorders, including cystic fibrosis, bronchitis, and emphysema using calf thymus DNA (Sigma, St. Louis). In each case, patients are administered sublingual drops of DNA at a concentration of about 0.0006 mg DNA per drop. No other therapy was conducted in any patient during the course of DNA therapy. As noted below, all patients tested showed improvement in mucus production (i.e. sputum was easier to dislodge) from the respiratory tract. In addition, sputum was less viscous as compared to pretreatment levels. Reduced sputum viscosity leads to increased patient comfort, increased ability of the patient to breathe, and reduced risk of secondary bacterial infection. No adverse side effects were observed in any patients. Drops of DNA may be administered at the appropriate concentration in doses of 1 to 10 drops per day as required by the patient. For each Example below, calf thymus DNA (Sigma) was used.

The following Examples illustrate the preferred embodiments of the invention and provide evidence of the effectiveness of claimed treatment methods. Numerous improvements and further aspects of the invention are apparent to the skilled artisan upon consideration of the Examples which follow.

EXAMPLE I

Twenty-three year-old twin brothers presented with cystic fibrosis. Each had a history of hospitalizations for lung clearance and secondary infections diagnosed as being associated with their cystic fibrosis. Each patient began therapy with 1–2 drops (0.0006 mg/drop) of DNA sublingually per day in November, 1993. For almost two years since beginning DNA therapy, neither patient has been hospitalized. In addition, follow-up evaluations by physicians revealed a 30–45% increase in airflow in each patient. Moreover, forced vital capacity, a common measure of lung capacity and the extent of mucus clearance in the lungs, increased from 60–90%. Finally, each of the brothers has gained weight and has shown increased expectoration.

After approximately one year of therapy, one of the brothers stopped taking the DNA drops. His condition steadily worsened as a result, with increased mucus viscosity, decreased forced vital capacity and reduced expectoration. That patient then began taking drops of DNA at the prescribed dose and immediately improved to the condition he was in prior to the time at which he stopped taking the drops.

EXAMPLE II

A 64-year-old female patient who suffered from emphysema and bronchitis, as diagnosed by her physician, was placed on a dose of 1 drop per day (0.0006 mg/drop) of DNA sublingually. Within one week, a follow-up evaluation revealed that her mucus production was less viscous and expectoration was increased.

EXAMPLE III

A 25-year-old female diagnosed with chronic upper respiratory illness was treated with methods according to the invention. Previous antibiotic therapy was unsuccessful in treating her condition. She began with 1 drop of DNA (0.0006 mg/drop) sublingually four times per day. Within one day, she experienced an increase in expectoration and, after three days she was able to discontinue treatment, having been completely relieved of congestion. She has remained symptom free.

EXAMPLE IV

A 32-year-old female nurse presented with a severe upper respiratory infection and unproductive respiratory congestion. She was placed on 1 drop of DNA (0.0006 mg/drop) four times per day. Her congestion began to break up almost immediately. Expectoration was improved and the patient's illness resolved after 4.5 days and no congestion recurred.

EXAMPLE V

A 63-year-old woman presented with chronic sinusitis. Four drops of DNA per day were administered. After 3 months, the patient's mucus had thinned and her cough was more productive.

EXAMPLE VI

A 37-year-old female presented with unresolved respiratory congestion. Traditional therapy, including expectorants, failed to improve her condition. The patient was then prescribed four drops of DNA (0.0006 mg/drop) per day. After one day of treatment, her congestion was more productive and sinus drainage had begun where none was present prior to treatment according to the invention.

EXAMPLE VII

A 40-year-old woman with unproductive upper respiratory congestion was placed on 4 drops of DNA (0.0006 mg/drop) per day. Her congestion was more productive after one day and she continued to expectorate freely. In this case, therapy was supplemented with an over-the-counter expectorant.

EXAMPLE VIII

A 38-year-old woman with acute and chronic respiratory disease due to exposure to toxic corrosive materials was treated with methods according to the invention. Prior to such treatment, symptoms, including chronic rhinorrhea, chest congestion and chronic respiratory infections were treated with numerous courses of antibiotics without success. The patient began treatment with 0.5 cc Q.I.D. daily and was instructed to administer treatment up to 5–6 times daily if necessary.

Upon commencing treatment according to the invention, the patient was able to produce sputum almost immediately. Continued treatment has alleviated symptoms of chronic respiratory illness.

EXAMPLE IX

A 58-year-old woman diagnosed with a childhood history of asthma and persistent adult rhinitis and sinusitis presented for treatment. Physical examination indicated clear rhinorrhea, and 3+ red throat. Nasal spray and prednisone were prescribed for 7 days. That course of treatment resulted in mild improvement. However, the patient's cough was still unproductive. Therapy according to the invention was begun at 0.5 cc Q.I.D. Within 48 hours, the patient showed improvement in the form of a productive cough and sinus drainage.

EXAMPLE X

A 48-year-old woman with chronic sinusitis and bronchitis characterized by chronic head congestion, nasal obstruction, and coughing presented for treatment according to the invention. The patient was treated according to the invention with one drop per day of DNA (0.0006 mg/drop). Treatment resulted in an overt increase in sinus and chest drainage. Upon cessation of treatment according to the invention, the patient's condition regressed. Beginning therapy again caused a similar increase in drainage and relief of congestion as seen previously with treatment according to the invention.

The invention has been described in terms of its preferred embodiments and is only invented to be limited by the scope of the following claims.

I claim:

1. A method for relieving respiratory congestion in a patient, comprising the step of administering sublingually and in a manner so as not to effect gene transfer and expression, a therapeutically effective amount of DNA in a pharmaceutically acceptable vehicle to a patient having a disease characterized by respiratory congestion, wherein said respiratory congestion is a result of an overproduction of viscous mucus or sputum lodged in said patient's respiratory tract, and wherein said method results in the reduced viscosity of said mucus or said sputum such that there is an increase of production and a reduced accumulation of mucus in said patient's respiratory tract.

2. The method according to claim 1, wherein said DNA is administered sublingually in the form of a liquid drop.

3. The method according to claim 1, wherein said disease is selected from the group consisting of cystic fibrosis, emphysema, bronchitis, and sinusitis.

4. The method according to claim 1, wherein said vehicle is selected from the group consisting of water, saline, albumin, or dextrose.

5. The method according to claim 1, wherein said effective amount of DNA is from about 0.00012 mg to about 0.003 mg DNA.

6. The method according to claim 1, wherein said effective amount of DNA is about 0.0006 mg of DNA.

7. The method according to claim 1, wherein said patient is a human.

* * * * *

UNITED STATES PATENT AND TRADEMARK OFFICE
CERTIFICATE OF CORRECTION

PATENT NO. : 5,726,160
DATED : March 10, 1998
INVENTOR(S) : John McMichael

It is certified that error appears in the above-identified patent and that said Letters Patent is hereby corrected as shown below:

Column 4, line 47, "or dextrose" should be --and dextrose--.

Signed and Sealed this

Thirteenth Day of February, 2001

Attest:

NICHOLAS P. GODICI

Attesting Officer

Acting Director of the United States Patent and Trademark Office